(12) United States Patent
Solo-Gabriele et al.

(10) Patent No.: US 8,053,241 B2
(45) Date of Patent: Nov. 8, 2011

(54) ARSENIC-SPECIFIC STAIN FOR IDENTIFYING ARSENIC-TREATED WOOD

(75) Inventors: Helena M. Solo-Gabriele, Miami, FL (US); Amy L. Omae, Fountain Valley, CA (US); Timothy G. Townsend, Gainesville, FL (US)

(73) Assignee: The University of Miami, Miami, FL (US)

( * ) Notice: Subject to any disclaimer, the term of this patent is extended or adjusted under 35 U.S.C. 154(b) by 529 days.

(21) Appl. No.: 12/091,444

(22) PCT Filed: Oct. 24, 2006

(86) PCT No.: PCT/US2006/041393
§ 371 (c)(1),
(2), (4) Date: Apr. 24, 2008

(87) PCT Pub. No.: WO2007/050562
PCT Pub. Date: May 3, 2007

(65) Prior Publication Data
US 2008/0280375 A1    Nov. 13, 2008

Related U.S. Application Data

(60) Provisional application No. 60/729,216, filed on Oct. 24, 2005.

(51) Int. Cl.
*G01N 33/20* (2006.01)
(52) U.S. Cl. ......................................................... 436/73
(58) Field of Classification Search .................... 436/73
See application file for complete search history.

(56) References Cited

U.S. PATENT DOCUMENTS 5,330,917 A   7/1994  Stone

FOREIGN PATENT DOCUMENTS

SU           373599        3/1970

OTHER PUBLICATIONS

Truog, E., A.H. Meyer, Improvments in the Deige Colormetric Method for Phosphorous and Arsenic, Mar. 1, 1929, Analytical Edition, vol. 1, No. 3, pp. 136-139.*
Lepage "Chemical methods for the determination of preservatives in wood" *Instituto de Pesquisas Tecnologicas Sao Paolo-Brasil*, Publication No. 893, pp. 49-65 (1970).
Chen et al. "Methods for rapid multi-element analysis in the field and their applications IV. Determination of arsenic and cadmium" *Rock and Mineral Analysis*, vol. 23, No. 1, pp. 25-28 (Mar. 2004).
Anchieta et al. "Spectrophotometric detection of arsenic using flow-injection hydride generation following sorbent extraction preconcentration" *Talanta*, vol. 50, pp. 959-966 (1999).
Khan et al. "Arsenic speciation of solvent-extracted leachate from new and weathered CCA-treated wood" *Environmental Science & Technology*, vol. 38, pp. 4527-4534 (Jul. 2004).
Int'l Search Report for PCT/US2006/041393.
Written Opinion for PCT/US2006/041393 mailed Mar. 27, 2007.

* cited by examiner

*Primary Examiner* — Jill Warden
*Assistant Examiner* — Monique Cole
(74) *Attorney, Agent, or Firm* — Nixon & Vanderhye P.C.

(57) ABSTRACT

A novel reagent is used to identify arsenic-treated wood. The stain may detect arsenic extracted from wood into solution; arsenic transferred from wood to a wipe, which is then extracted into solution; or the stain may be directly applied at a predetermined location on the wood's surface. Copper preservatives are not detected by the stain and phosphate interference is minimized. The process is quick, inexpensive, and easy to use. Development of a blue color (i.e., reduction of at least some Mo (VI) to Mo (V) in molybdenum blue) indicates the presence of arsenic.

13 Claims, No Drawings

ARSENIC-SPECIFIC STAIN FOR IDENTIFYING ARSENIC-TREATED WOOD

CROSS REFERENCE TO RELATED APPLICATIONS

This is a U.S. national phase of Intl Patent Application No. PCT/US2006/041393, filed 24 October 2006, which designated the U.S. and claims priority to U.S. Provisional Patent Application No. 60/1729,216, filed 24 October 2005; the entire contents of each of which are hereby incorporated by reference.

BACKGROUND OF THE INVENTION

The invention relates to arsenic-specific stains, kits for detecting arsenic, and processes for detecting arsenic. Arsenic-treated wood is identified thereby with minimal interference from phosphate. Processes for making arsenic-specific stains are also provided.

Preservative chemicals are added to wood products in order to prevent their biological deterioration from insects and fungi. In warm and humid climates, wood exposed to the outdoor environment will last only one to two years but its structural integrity can be maintained through 25 to 40 years by chemical treatment (Stalker, 1993; Cooper, 1993). Durability will depend upon the amount of chemical added to the wood, its use, and local climate conditions. A term used by the wood treatment industry to describe the amount of chemical added is "retention." The lower the retention, the lower the amount of chemical added to the wood per unit volume of wood. Treatment at lower retention levels is used for wood intended for above ground and ground contact applications, whereas treatment at higher retention levels is used for wood intended as load-bearing supports for a structural member or for marine submersion (AWPA, 2003).

Wood preservatives can be separated into two broad categories: oilborne preservatives and waterborne preservatives (Milton, 1995). Wood treated with oil-borne preservatives are almost exclusively utilized for outdoor industrial applications since they are oily to the touch and in many cases have odors associated with them. The waterborne wood preservatives, also known as metal-based preservatives, are typically composed of metal oxides and, in some cases, an added organic co-biocide. Treated wood used in residential applications is almost exclusively treated with waterborne preservatives. Wood treated with waterborne preservatives is preferred for residential applications because, in contrast to their oilborne counterparts, the product can be painted, does not have an odor, and is dry to the touch.

Within the U.S., the metals typically used in wood preservative formulations include copper, chromium, arsenic, and boron (AWPA, 2003). The most common wood preservative through the 1980's and 1990's contained arsenic and included, predominantly, chromated copper arsenate (CCA) and, secondarily, acid copper zinc arsenate (ACZA) (AWPI, 1996; Micklewright, 1998). As of Jan. 2, 2004, the wood treatment industry voluntarily withdrew from manufacturing arsenic-treated wood for products intended for most residential uses (EPA, 2002). Exemptions to the ban include lumber and timber for salt water use only, piles, poles, plywood, wood for highway construction, poles/piles/posts used as structural members on farms and plywood used on farms, wood for marine construction, round poles/posts used in building construction, sawn timber used to support residential and commercial structures, sawn crossarms, structural glue laminated members and laminations before gluing, structural composite lumber, and shakes and shingles. Thus, the phase out will not result in the complete absence of arsenic-treated wood because the products listed above will likely continue to be treated with CCA or AZCA.

Phase out of arsenic-treated wood was initiated, in part, by growing public concerns about the possible adverse health effects associated with the arsenic contained in treated wood and with the advent of non-arsenic alternatives. Exposure to the chemicals contained in treated wood may occur directly through contact with the wood surface (Shibata et al., 2004; Stilwell, 2003; U.S. CPSC, 2003; ACC, 2003) or indirectly due to the leaching of the chemicals from the wood and subsequent environmental contamination (Stilwell & Gorny, 1997; Townsend et al., 2003a). The alternatives to CCA and ACZA typically contain higher concentrations of copper and an organic co-biocide. These alternatives do not contain arsenic as an active ingredient and so the concentration of arsenic within the treated wood product is low, typically near background concentrations for untreated wood (Table 1). Commercially available copper-based alternatives that can be used in residential outdoor settings include: alkaline copper quat (ACQ) and copper boron azole (CBA). In the past, other copper-based preservatives that have been sold in relatively small quantities in the U.S. include copper citrate (CC) and copper dimethydithiocarbamate (CDDC). Currently, the CC and CDDC alternatives are not marketed in the U.S. Borate-treated wood products are generally replacing CCA-treated wood in areas where treated wood is used indoors for added termite protection. Borate-treated wood is not recommended for outdoor use (AWPA, 2003) due to its tendency to leach out of the wood when wet. Some borate-treated products are generally well-fixed to the wood. The borate in these products is typically added in an insoluble powder form as zinc borate. Because the borate is added as a solid, treatment is limited to composite wood products such as oriented strand board, particleboard, and flakeboard. Since copper and boron are considered to be significantly less toxic to humans than arsenic, the alternatives are considered to be more environmentally acceptable and more favorable when contact with humans is likely. Concerns have been raised however due to the higher aquatic toxicity of copper relative to arsenic (Weis & Weis, 1995; Stook et al., 2004). Wood treated with copper-based alternatives is not recommended within sensitive aquatic environments (Stook et al., 2005).

TABLE 1

Metal Concentrations of Common Metal-Based Preservatives in Comparison to Untreated Wood.

| Metal Preservative | Untreated Wood | Above Ground Retention Levels | | | | Indoor Use Inorganic | Retention Levels for Marine Submersion[b] |
| --- | --- | --- | --- | --- | --- | --- | --- |
| | | CCA (4 kg/m$^3$) | ACZA (4 kg/m$^3$) | ACQ (4 kg/m$^3$) | CBA (3.3 kg/m$^3$) | Boron (4.5 kg/m$^{3,e}$) | CCA (40 kg/m$^3$) |
| Arsenic, mg/kg[a] | <8 | 1,800 | 1,300 | NA[c] | NA | NA | 18,000 |
| Chromium, mg/kg | <22 | 2,000 | NA | NA | NA | NA | 20,000 |
| Copper, mg/kg | <4 | 1,200 | 3,100 | 4,300 | 3,200 | NA | 12,000 |
| Zinc, mg/kg | — | NA | 1,600 | NA | NA | NA | NA |
| Boron, mg/kg | — | NA | NA | NA[d] | 570 | 2,800 | NA |

[a] mg of metal per kilogram of wood. Concentrations were computed using the typical density of Southern Yellow Pine of 500 kg/m$^3$ (AWPA, 2003).
[b] ACQ-, CBA- and borate-treated wood not standardized for marine submersion. ACZA is standardized for marine submersion.
[c] NA = Not an active ingredient added to the wood.
[d] Boron is added to the ACQ formulation as an anti-corrosion agent. It is not added as an active ingredient.
[e] Retention level corresponds to formulation providing resistance to Formosan termites.

Although the manufacture of CCA-treated wood for residential applications has been greatly restricted as of 2004, there still exists a large inventory of CCA-treated wood currently in use due to the long service life of the treated wood product (Solo-Gabriele & Townsend, 1999). As a result of this inventory, there is a need to identify whether arsenic-treated wood is contained within existing structures so toxic exposure can be reduced. For example, recent risk assessments indicate that children who routinely play on CCA-treated playground equipment and decks may increase their risk of cancer by a margin greater than the acceptable 1 per million level due to the possible ingestion of arsenic from surface residues on treated wood (Roberts & Ochoa, 2001; CPSC, 2003; Maas et al., 2004; Dang et al., 2003). In such situations, in particular for structures frequented by children, it will be important to determine whether or not the wood contains arsenic so that measures can be taken to remediate existing wood structures. Remediation may include coating the structure with an oil-based penetrating stain (Stilwell, 1998; Feist & Ross, 1995; Maas et al., 2002; Lebow et al., 2003; Cooper et al., 1995; Cooper & Ung, 1997; EPA, 2004). Other concerns may arise when existing structures undergo cleaning and painting for aesthetic reasons. In such cases it would be helpful to know what chemicals are contained within the wood so that proper safety equipment is utilized and that care is taken in choosing the appropriate cleaners for the wood, since some oxidant-based cleaning products have a tendency to convert the chromium within CCA to a more toxic form (Taylor et al., 1998).

In addition to identifying CCA within structures that are currently being used, CCA-treated wood should be properly identified during its disposal. In Florida, construction and demolition (C&D) wood is in many cases recycled into consumer mulches (Tolaymat et al., 2000). C&D wood mulch must be essentially free from arsenic-treated wood in order for it to pass regulatory guidelines for recycling (Townsend et al., 2003b). But assuring that C&D wood mulch is free from CCA is not easy since it requires the rapid identification of chemical treatment during sorting. Also, care must be taken when disposing of CCA-treated wood within landfills. CCA-treated wood should be preferentially disposed within landfills that have bottom liners versus those that do not. In such cases, metals that leach from CCA-treated wood during its decomposition can be captured by the bottom liner and can be subsequently managed, versus the uncontrolled loss of the metals from unlined landfills. In many instances, the ultimate disposal of wood is through combustion (Solo-Gabriele & Townsend, 1999). Combustion may occur within mass burn solid waste facilities, or in facilities capable of recovering energy during the combustion processes. In either case, it will be important for wood-burning facilities to control their incoming waste/fuel stream in order to better manage air emissions and resulting ash quality. This is true for all treated wood but, in particular, wood treated with arsenic-containing preservatives since metals like arsenic are not decomposed. During combustion, the metals are usually concentrated in the ash or lost through air emissions in the event that air pollution control devices are not employed. Identification of preservatives contained within wood is thus important during disposal.

Another practical issue that requires the identification of treated wood products is the need for special fastener systems for wood treated with ACQ. ACQ-treated wood is generally more corrosive to metal fastener systems than CCA-treated wood (CSI, 1995), requiring either stainless steel or hot-dipped galvanized metal fasteners. As a result, during the construction process, it will be important to properly segregate ACQ-treated wood from CCA-treated wood so that the proper fastener systems can be utilized with each wood product. The need for such sorting was emphasized when a south Florida homebuilder's stockpiles of ACQ-treated wood were inadvertently, mixed with CCA-treated wood. There was a need to sort the stockpiles and reconfirm whether existing structures were constructed of CCA- or ACQ-treated wood to assure that the correct fasteners were used.

We focus on processes to identify whether or not wood is treated with arsenic-containing preservatives. Visualization techniques that can be utilized by simply looking at the shape and color of the wood to make an initial judgment concerning whether or not it is treated. Since simple visual techniques are not always accurate, augmentation technologies can be employed in the field for rapid identification of the metals contained in treated wood. Rapid identification techniques include the use of chemical stains, arsenic test kits, x-ray, and laser technologies. We describe a stain which is arsenate specific, minimizes interference by phosphate, and can quickly and inexpensively detect arsenic-treated wood in the field.

Visualization Techniques

When approaching wood which was used in outdoor structures or applicable indoor settings, the initial assumption is to consider it treated. When observing wood in the disposal stream, look for evidence that the disposed wood was part of a fence or a dock. This is readily observable when the structures have not been completely demolished upon arrival at the disposal facility. If the origin of the wood is not readily noted, look for end tags which may still be present on construction wood. These end tags will indicate the preservative used to treat the wood. The presence of barnacles on wood will indicate that it was used in marine applications and is likely treated. If the wood is incised, it is also treated. Incising is a process by which uniform cuts are made in the wood to improve the penetration of the preservative during treatment. Treated industrial wood products can usually be identified based upon their large dimensions. For example the typical dimensions of railroad ties are 0.2 m×0.2 m×2.6 m, and utility poles are typically 30 cm in diameter. Both industrial products are almost exclusively treated. In some cases, landscape timbers can be identified by their shape which in many cases is characterized by rounded edges for decorative purposes. Size and shape of wood is not a very good indicator of treatment for most residential wood which is primarily composed of lumbers, timbers, and plywood. Lumbers, timbers, and plywood can be found either treated or untreated, so identification of treated wood among wood products with these dimensions is more difficult.

Another simple visual method that can be used to preliminarily identify treated wood is to look at the color of the wood. Different wood species are characterized by different colors. The most common wood species used for treatment in the southern, northern, and midwestern U.S. is Southern Yellow Pine (SYP), which is naturally yellow in color. When SYP is treated with a preservative such as CCA, ACQ, or CBA, the color can vary from a light olive green to an intense green depending upon the amount of preservative added to the wood. The green color is due to the copper, which for wood treated at low retention levels can correspond to a very subtle color differential. Another distinct color change is observed for ACZA-treated Douglas Fir. In addition to incisions made during treatment, ACZA tends to react with specific compounds in Douglas Fir to produce a dark brown color, which is readily identifiable within the disposal sector (Ruddick & Xie, 1994).

Once the wood has been in-service and is weathered, the olive-green color from copper treatment is maintained only for wood treated at high retention levels (e.g., 40 kg/m$^3$). The color of wood treated at low retention levels (e.g., 4 kg/m$^3$) will change to a silver color upon weathering. This change in color occurs after only a year or two of weathering. Untreated wood generally weathers to the same silver color. As a result, identification of treated SYP wood based on color alone is difficult, in particular if the wood is weathered and was originally treated at a low retention level. Visual identification of copper-treated treated wood is further hampered if the wood comes from a demolition facility since dust and dirt will tend to mask the subtle green color of low retention level wood.

Because of limitations on visualization techniques for detecting treated wood, augmentation techniques are used to identify wood treated with copper or arsenic preservatives.

Augmentation Techniques

The simple visualization techniques described above are not accurate enough for identifying treated wood. Due to the phase-out of CCA-treated wood, more and more residential structures are being constructed of wood treated with non-arsenic copper-based alternatives (e.g., ACQ and CBA). Due to concerns associated with the toxicity of arsenic and the different fastener systems that are recommended for each of these wood types, there will be a growing need to improve methods by which CCA-treated wood can be distinguished from CBA- and ACQ-treated wood. CCA-, CBA-, and ACQ-treated wood are all olive-green in color and visual identification of each wood type (in the absence of end tags) is almost impossible. Limitations of visual sorting methods are further emphasized through studies by Blassino et al. (2002) who documented the quality of the "recyclable" wood piles at three C&D recycling facilities located in Florida. Two facilities practiced visual sorting and one did not. The two facilities that practiced visual sorting had between 9% and 10% CCA-treated wood, by weight, within their "untreated" wood pile, whereas the remaining facility had 30% CCA-treated wood in their wood pile. Although the number of C&D facilities evaluated by Blassino et al. (2002) was small, their study suggested that visual sorting does improve the quality of sorted wood and can potentially decrease the amount of CCA-treated wood entering the waste stream by about 60% to 70%. Furthermore, Blassino et al. (2002) visually sorted waste loads from a C&D facility based upon only the color and shape of the waste wood and then checked the accuracy of their sorts. The results of their study showed that visual sorting based upon the size and color of the wood correctly identified wood as "CCA treated" or "not CCA treated" 90% of the time, on average. Incorrect determinations occurred 10% of the time. Although visual sorting based on color and shape of the wood improves the quality of waste wood, such sorting is not accurate enough for assuring a wood waste essentially free of arsenic-treated wood.

There are several methods to augment the identification of wood treated with copper- and arsenic-containing preservatives (Homan & Militz, 1994). Many of them require laboratory analysis and are not suitable for field use. Typically, sawdust samples are provided to a laboratory which then processes the samples by dissolving the sawdust in an acidic solution and then the acidic solution is analyzed using sophisticated laboratory equipment (such as an atomic absorption spectrometer or inductively-coupled plasma atomic emission spectroscopy). If the sawdust sample is found to contain arsenic concentrations on the order of several hundred mg/kg or greater, then it has been treated with an arsenic-containing preservative. But laboratory analyses are expensive (typically on the order of $50 per sample) and require several days to weeks to obtain results.

Other more rapid methods for identifying treated wood can be separated into two categories: those characterized by low capital cost but are highly labor intensive and those that are semi-automated and characterized by high capital costs. Analysis times for labor intensive methods (e.g., PAN stain and generation/detection of arsine gas with a water test kit) vary from many seconds to many minutes. The analysis times for the semi-automated systems (e.g., laser and x-ray technologies) are typically on the order of a fraction of a second. These labor intensive methods use chemical stains or metal test kits, which readily identify the presence of a particular chemical. The cost of analysis by chemical stain or test kit is typically a fraction of a dollar per sample. The less labor-intensive semi-automated methods require the purchase of expensive equipment (many thousands of dollars). Such technologies are currently being evaluated for their potential to augment existing sorting techniques (based upon the green hue of treated wood) and to sort large quantities of wood using conveyor systems.

PAN stain is found to quickly react and creates a distinct color that could be readily identified in the field (Blassino et al., 2002). PAN is the abbreviation for the chemical 1-2(-pyridylazo)-2-napththol, an orange-red solid with a molecular formula of $C_{15}H_{11}N_3O$ (McMurry, 1992; Sandell & Onishi, 1978). It is used to determine the presence of almost all metals (40 to 50 in total), excluding alkali metals such as arsenic. During the reaction between a metal and PAN indicator, the metal bonds to the oxygen of the OH— group by replacing the hydrogen atom, and to pyridine and azo nitrogen atoms (Sandell & Onishi, 1978). The reaction with the non-alkali metals in CCA-treated wood produces color that is magenta to red; untreated wood turns orange in color.

A readily-available test kit (Product 17926, EM Science, Gibbstown, N.J.) is modified for the detection of arsenic in treated wood samples. The test kit utilized is sold commercially for analyzing arsenic in drinking water. Use of the kit is modified by adding a sawdust sample from the structure to be evaluated to a test tube. Water is then added to the test tube and chemicals that come with the kit (zinc and HCl) are added to the sawdust-and-water solution. The addition of these chemicals converts arsenic within the sawdust-and-water solution to arsine gas. This gas then reacts with a test strip (impregnated with mercury (II) bromide) to result in a color change from white to brown or black. In all cases, results from the arsenic test kit are consistent with the results from the laboratory analysis from the same structures. The test kit consistently provided positive readings for CCA-treated wood structures (ranging in concentration from 1400 to 3800 mg/kg As) and negative readings for structures made from untreated wood or non-arsenical copper-treated wood (less than 3 mg/kg As). The major drawbacks associated with this method are the need for laborious sample processing and the generation of toxic gas. As a result, this method may be used for evaluating only one or two structures in the field. This method is also not recommended for use by those inexperienced with the handling of chemicals, due to the use of toxic chemicals and the formation of arsine gas. It is likely that arsine gas generated from the analysis of treated wood samples is greater than the generation from drinking water samples due to the higher concentration of arsenic from the sawdust.

Laser induced breakdown spectroscopy (LIBS) is extremely rapid and can easily operate at 10 Hz (ten readings per second). A high-powered laser is directed towards the sample to create a spark (plasma flash) which vaporizes a small portion of the surface of the wood, provided that it is within a set distance (focal length) from the laser housing. The atoms within the plasma emit light characterized by different wavelengths; certain wavelengths of emitted light are unique to different elements in a phenomenon called atomic emission. Intensity of the emission is directly proportional to the amount of that element present in the original wood sample (Radziemski & Cremers, 1989). A pilot scale LIBS system was constructed and tested for sorting treated wood waste (Solo-Gabriele et al., 2004; Solo-Gabriele et al., 2001; Moskal & Hahn, 2002; Moskal, 2001). Once any coating is stripped away through successive laser pulses on the same area, LIBS could detect whether or not the wood sample was CCA treated. Excessive moisture in the wood interfered with the ability of the system to detect CCA-treated wood. Although the system is capable of detecting CCA on damp wood, it is not capable of detecting treatment on wood after it had been soaked in water.

X-ray fluorescence spectroscopy (XRF) has been used by the wood treatment industry as a means of checking the quality of the treated wood product (AWPA, 2003). Blassino et al. (2002) documented operating parameters from trials in the laboratory. These trials indicate that XRF can detect the presence of chromium, copper, and arsenic with arsenic providing the strongest signal among the three. The metals were detected even for the wood samples characterized by the lowest CCA retention levels (4 kg/m$^3$). The same instrument was field tested at a C&D debris processing facility located in Sarasota County, FL (Solo-Gabriele et al., 2004).

But LIBS and XRF require expensive instrumentation and this limits the availability of detection to the locations where the instruments are located. Moreover, users of the instruments must be trained in their sophisticated operation. Such factors limit their widespread use for detecting arsenic-treated wood.

Therefore, it is an objective of the invention to provide a novel reagent for use as an arsenic-specific stain to detect arsenate extracted from wood suspected of being treated with preservative(s). The present invention is directed to an improved process for detecting arsenate in wood that addresses the aforementioned problems. It is quick, inexpensive, and non-sophisticated users are able to successfully segregate arsenic-treated wood (e.g., CCA or ACZA preservative). Other advantages and improvements are described below or would be apparent from the disclosure herein.

SUMMARY OF THE INVENTION

The invention is used to detect arsenic-treated wood. Arsenic contained in a wood sample may be extracted into solution and a blue color developed with stain; or the stain may be directly applied at a predetermined location on the wood sample's surface; or arsenic may be sampled from wood and transferred to a wipe, extracted into solution from the wipe, and developed with the stain. The invention provides a process for detecting arsenic in weathered or unweathered wood suspected of being treated with an arsenic-containing preservative.

Arsenic contained in wood is detected by a method using ammonium molybdate and stannous chloride. Sawdust, shredded wood, or wood chips, or intact wood suspected of being treated with preservative may be processed. Wood residue may be transferred from the wood's surface to a wipe, and then processed. An interior surface of the wood may be exposed, and then processed. Arsenic from the wood or wood product reacts with ammonium molybdate and stannous chloride, and the presence of arsenic is detected by development of blue stained wood or blue color in solution (i.e., molybdenum blue).

In the reaction, the concentration of ammonium molybdate may be at least 0.01 mM, at least 0.1 mM, at least 0.5 mM, at least 2 mM, at most 5 mM, at most 10 mM, at most 50 mM, at most 100 mM, from 0.01 mM to 5 mM, from 2 mM to 100 mM, or an intermediate range thereof and the concentration of stannous chloride may be at least 0.005 mM, at least 0.01 mM, at least 0.1 mM, at most 0.5 mM, at most 1 mM, at most 5 mM, at most 10 mM, from 0.005 mM to 0.5 mM, from 0.1 mM to 10 mM, or an intermediate range thereof.

Detection occurs in 10 minutes, 15 minutes, 30 minutes, 45 minutes, 1 hour, 2 hours, 3 hours, 4 hours, 5 hours, 6 hours, or intermediate ranges thereof (e.g., 10 minutes to 6 hours). Two milligrams, 4 milligrams, or 8 milligrams of arsenate per liter of solution can be detected; 2 kilograms, 4 kilograms, or 8 kilograms of arsenic-containing preservative (e.g., chromated copper arsenate, acid copper zinc arsenate) per cubic meter of wood can be detected.

A kit for detecting arsenic comprised of one or more containers in a package is provided, which includes: a first reagent comprised of ammonium molybdate and a second reagent comprised of stannous chloride. Optional components of the kit include one or more of the following: a positive control containing arsenate, a negative control containing phosphate and/or not containing arsenate, and at least one known amount of arsenate for calibrating the amount of preservative which can be detected using the kit. Instructions for processing wood samples may be included in the kit.

An arsenic-specific stain comprised of ammonium molybdate and stannous chloride is provided; also provided are processes for making the stain by mixing ammonium molybdate and stannous chloride. Volumes of ammonium molybdate to stannous chloride in a ratio of about 1:8 (e.g., at least 6:1, at least 7:1, at most 9:1, at most 10:1, from 7:1 to 9:1, from 6:1 to 10:1, or intermediate ranges thereof) may be used for the stain. Alternatively, the molar ratio of ammonium molybdate to stannous chloride in the stain may be about 1.46:1 (e.g., at least 1.0:1, at least 1.1:1, at least 1.2:1, at least 1.3:1, at least 1.4:1, at most 1.5:1, at most 1.6:1, at most 1.7:1, at most 1.8:1, at most 1.9:1, from 1.4:1 to 1.5:1, from 1.3:1 to 1.6:1, from 1.2:1 to 1.7:1, from 1.1:1 to 1.8:1, from 1.0:1 to 1.9:1, or intermediate ranges thereof).

Further aspects of the invention will be apparent to a person skilled in the art from the following description of specific embodiments and the claims, and generalizations thereto.

DESCRIPTION OF SPECIFIC EMBODIMENTS OF THE INVENTION

The present invention is a modification of a colorimetric method used to detect the presence of phosphate in water. Initial evaluation of the two phosphate methods (stannous chloride and ascorbic acid stains) for detecting arsenate in wood were promising. Arsenic in treated wood is primarily present as arsenate ($AsO_4^{3-}$), which has a chemical form similar to phosphate ($PO_4^{3-}$). The predominance of arsenate within CCA is due to the fact that the original CCA solution is composed of arsenate compounds. Some evidence suggests that arsenate may be converted to arsenite ($AsO_3^{3-}$), as observed in leachates from treated wood but this conversion corresponds to less than 20% in the majority of cases (Khan et al., 2004). Methods used to evaluate phosphate in water could therefore be used to detect the presence of arsenic in wood. Both phosphate methods (i.e., stannous chloride and ascorbic acid stains) resulted in a blue color if arsenic was present in the wood. Both methods, however, suffered from interference reactions for untreated wood, resulting in a blue color for untreated wood, presumably due to the presence of detectable levels of phosphate in untreated wood (about 1.4 mg/L to 1.8 mg/L leaching out after soaking for 12 hours). This interference was minimized for the stannous chloride method (APHA, Method 4500-P D) and it was therefore the focus of subsequent evaluation. The stannous chloride method detects phosphate by the following chemical reactions:

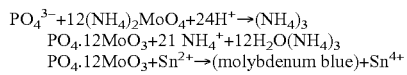

Therefore we modified this procedure to detect arsenic (i.e., indirectly through arsenate) by reducing ammonium molybdate with stannous chloride before staining and color development. This causes over-reduction of molybdenum and a reduced sensitivity for the detection of phosphate and arsenate. A phosphate concentration of about 1.8 mg/L is tolerated in the specific detection of arsenic. Development of a blue color with arsenic-treated wood samples is mostly due to the presence of arsenate. The phosphate naturally present in wood does not cause a noticeable blue color with the modified stain disclosed herein. Other sources of interference are not considered to be important because they are usually absent in wood and wood products. Therefore, no separation of arsenate from other substances (e.g., phosphate) or removal of other interfering substances prior to detection of arsenate is required.

The change in oxidation state of some of the stain's molybdenum is from +6 to +5. Molybdenum blue is a complex of 12 molybdate molecules surrounding a central ammonium arsenate molecule. Before the formation of molybdenum blue (i.e., color development), molybdenum is in the +6 oxidation state. Upon reduction, at least some molybdenum in the complex is reduced to the +5 oxidation state. The exact ratio of Mo (VI) to Mo (V) will vary according to reaction conditions but is not critical.

A kit may be provided comprised of one or more containers in a package with (i) ammonium molybdate, stannous chloride, or a mixture thereof and optionally one or more of (ii) a positive and/or negative control for staining and (iii) a calibration standard of a known amount(s) of arsenic. One or both solutions of ammonium molybdate and/or stannous chloride may be provided in the container(s) or be made in the field from components therein and a solvent. Other optional components of the kit include (iv) a means to bring stain in contact with wood (e.g., brush, pipet, or wipe), (v) a reaction vessel (e.g., trans-parent multiwell plate, vial), (vi) a means for sampling (e.g., abrasive, awl, knife, solvent, surfactant), and (vii) written instructions for performing the assay. One test, at least three tests, or at least ten tests may be performed with the reagents packaged in the kit. A light- and moisture-resistant wrapper may be used for long-term storage of the kit.

Visual inspection of a reaction site will detect at least the presence of arsenic by a change in color. The quantity of arsenic can be determined by comparing the developed color to a graduated color scale correlated to known amounts of arsenic, or measuring its absorbance with a spectrophotometer related to a standard curve of known amounts of arsenic.

Wood that may be suspected of containing arsenic may be "sampled" by applying stain to the wood's exterior, exposing an internal surface of the wood and applying stain to the exposed surface, soaking the wood in eluent to extract at least some arsenic that might be present, or treating chips or a powder of the wood as one would a liquid because arsenic is extracted into diluent rapidly due to the increased surface-to-volume ratio resulting from the decrease in the size of the wood.

Stain may detect the presence of arsenic in a wood sample by "painting" the stain on the sample's exterior and allowing the reaction to develop color. But the wood's exterior might not be representative of the sample because of exposure to the environment (e.g., rain, soil, sun, sea) or preservative coating (e.g., paint, resin, sealants). In such situations, the exterior may be cleaned (e.g., with a solution containing surfactants and/or solvents), an internal surface may be exposed (e.g., boring with an awl, sanding with an abrasive, shaving with a knife), or the wood may be made into chips or a powder. The processed piece of wood may then be sampled as described above.

EXAMPLES

A dissolution method was developed by us in order to use the modified stannous chloride stain to detect arsenic in wood. This requires obtaining a wood product suitable for extracting any arsenate present therein into an aqueous solution, placing the wood in a vial which contains water and the stain, and then observing whether there is any color change of the vial's solution. Only solutions with a CCA-treated wood sample mixed in an aqueous carrier containing stain turned blue in color. Solutions containing a sample from untreated or non-arsenic preservative (e.g., CC, CDDC, CBA, ACQ, borate) treated wood remained colorless or light brown in color after mixing with stain. In this manner, at least some arsenate present in wood is extracted into solution where the blue color is more easily seen and there is less interference from phosphate. The development of blue color indicates the sample contained arsenate; any color other than blue, most commonly clear, yellow, brown, and beige, indicates the absence of arsenate (or at least below the limits of detection).

Alternatively, a wipe (e.g., woven or non-woven fiber) may be used to transfer arsenic from a wood surface to the wipe. For example, a clean location on the wood is repeatedly rubbed with the wipe along the grain to collect wood residue; a white or light-colored wipe is darkened as residue is collected on the wipe, and then the wipe is trimmed so that portions of the wipe which has not collected wood residue can be discarded. Any arsenate on the wipe was extracted into solution after placing the wipe in a vial which contains the stain, and then observing whether there is any color change of the vial's solution. Only solutions with wipes from arsenic-treated wood mixed with stain turned blue in color. In this manner, at least arsenate present in wood is extracted into solution where the blue color is more easily seen and there is less interference from phosphate. The development of blue color indicates the wood contained arsenate; any color other than blue, most commonly clear, yellow, brown, or beige, indicates the absence of arsenate (or at least below the limits of detection).

Our procedure may also be used by obtaining an unweathered wood sample, directly applying the stain on the wood's surface, and then observing whether there is any color change in the stain. Alternatively, an interior surface of a weathered wood sample may be exposed prior to processing to avoid inaccurate results (e.g., false negative from difference between exterior and interior) or sampling other non-wood substances (e.g., coating or soiling) which accumulate on the exterior surface. For example, shallow cutting(s) into the wood provides one or more thin slivers (shaving results in two interior surfaces, either of which may be processed by staining the exposed surface) or boring into the wood provides small particles or a solid narrow core (processed by either dispersing in solution or staining the exposed surface). When exposing an interior surface, the preservative should have had the opportunity to penetrate into the wood. CCA-treated wood developed blue stain; the appearance of wood which was untreated or non-arsenic preservative (e.g., borate, ACQ, CBA) treated wood remained the same (e.g., clear, yellow, brown, or beige due to the natural color of the wood).

Reagents

Ammonium molybdate reagent: Dissolve 25 g $(NH_4)_6Mo_7O_{24} \cdot 4H_2O$ (MW 1235.86) in 175 mL distilled water, cautiously add 280 mL concentrated $H_2SO_4$ to 400 mL distilled water and cool, mix molybdate and acid solutions, and dilute to 1 L. Final concentration is about 20.23 mM ammonium molybdate. The solution keeps indefinitely.

Stannous chloride reagent: Dissolve 2.5 g fresh $SnCl_2 \cdot 2H_2O$ (MW 225.63) in 100 mL glycerol, heat in a water bath, and stir with a glass rod to hasten dissolution. Final concentration is about 110.8 mM stannous chloride. This reagent is stable for at least 6 months, and requires neither preservatives nor special storage.

Combined reagent for "Dissolution Method": Prepare immediately prior to assaying by mixing 8 mL ammonium molybdate and 1 mL stannous chloride reagents. The volume ratio of ammonium molybdate and stannous chloride reagents may be increased or decreased, but a ratio of about 8:1 is strongly preferred.

Combined reagent for "Whole Wood Method": Prepare immediately prior to assaying by mixing 9 mL deionized water, 16 mL ammonium molybdate reagent, and 2 mL stannous chloride reagent. The volume ratio of ammonium molybdate and stannous chloride reagents may be increased or decreased, but the ratio of about 9:16:2 ratio is strongly preferred.

*NOTE: If the volume ratio of ammonium molybdate to stannous chloride is decreased from 8:1, development time may be lengthened while increasing the ratio may result in interference by phosphate. It is preferred to avoid allowing the combined reagent to stand for more than one hour because development time may be lengthened and color intensity may be weakened. A concentration of more than about 0.8 mg/L phosphate during development may result in interference with the arsenic-specific reaction.

Dissolution Method
a. Add about 10 mL distilled water to a 20-mL sample vial with cap.
b. Prepare the combined reagent. Mix and let stand for about 5 minutes.
c. Add about 0.45 mL combined reagent to the sample vial (a dilution factor of about 9:200). The resulting concentrations are about 0.774 mM ammonium molybdate and about 0.530 mM stannous chloride.
d. Add about 0.5 g of sawdust, shredded wood, or wood chips to the sample vial. Shake.
e. Wait about 30 to 45 minutes for color to develop. Shake occasionally.
f. Note the color of the solution. If the solution is clear, yellow, brown, or beige, then the wood is negative for arsenic. If the solution turns a light blue or blue-green color, then the wood is positive for arsenic.

*NOTE: The color change for the arsenic-specific stain is gradual. Therefore, if unsure about any possible color change within about 45 minutes, then it may be necessary to wait for a longer time period. The blue or blue-green color reaches its maximum intensity in about 5 hours for CCA-treated wood and in about 2 hours for ACZA-treated wood.

Whole Wood Method
a. Prepare the combined reagent. Mix and let stand for about 5 minutes.
b. Dilute combined reagent with deionized water at a ratio of about 18:9 (the resulting concentrations are about 11.99 mM ammonium molybdate and about 8.21 mM stannous chloride). Shake.
c. Apply to unweathered wood and let stand for about 90 minutes.
d. Wait about 30 to 90 minutes for color to develop.
e. Note the color of the location where the combined reagent is applied. If the color is brown or brown-gray, then the wood is negative for arsenic. If the area turns a blue or blue-gray color, then the wood is positive for arsenic.

*NOTE: The blue color reaches its maximum intensity in about 2 hours for CCA-treated wood. ACZA is commonly used to treat Douglas Fir and results in a dark brown color that would mask development of blue color, if it were to occur. Therefore, the "Whole Wood Method" is not preferred for ACZA-treated Douglas Fir.

Example 1

Arsenic Extracted from Wood

Untreated or non-arsenic preservative (e.g., CC, CDDC, CBA, ACQ, borate) treated wood was extracted into solution, the solution was mixed with ammonium molybdate and stannous chloride, and shaken in accordance with the "Dissolution Method" described above. No development of blue color was observed. But wood treated with 4.0 kg/m$^3$ CCA or ACZA preservative resulted in development of a blue color when processed in accordance with the "Dissolution Method" described above. Color reaches its maximum intensity in about 5 hours for CCA-treated wood and in about 2 hours for ACZA-treated wood.

Using sodium molybdate instead of ammonium molybdate in the "Dissolution Method" developed a blue color with untreated wood because of an undesirable reaction due to phosphate interference. Therefore, ammonium cation is preferred over alkali metal cations for the molybdate reagent. Similarly, while other reducing agents could be used, ammonium molybdate and ascorbic acid developed a blue color with untreated wood because of an undesirable reaction due to phosphate interference. Therefore, stannous chloride is preferred over ascorbic acid for the reducing reagent.

Parallel reactions with 4.0 kg/m$^3$ CCA-treated wood processed in accordance with the "Dissolution Method" described above were developed over 5-1/2 hours. Absorbance at 690 nm was zero at the beginning and increased to greater than 1.15 as a function of time. Serial dilutions of CCA-treated wood particles processed in accordance with the "Dissolution Method" described above showed that the detection limit was 2 mg/L arsenate.

Wood weathered by exposure to the outdoor environment was also processed by the "Dissolution Method" described above. A total of 33 weathered wood samples were evaluated. Nine were obtained from a wood recycling facility: seven non-arsenic treated samples (A to G) and two arsenic-treated samples (H and I) were all accurately determined by our method (Table 2). In the field, prior art methods like PAN staining and XRF were compared to use of the arsenic-specific stain (Table 2).

Twenty-four were obtained from playgrounds throughout south Florida. All were presumed to come from playgrounds built with arsenic-treated wood, but arsenic was detected in only 21 out of the 24 samples. The level of arsenic in the three negative samples was very low and yielded less than 2 mg/L of arsenate with more sensitive techniques. The retention level of these three samples was measured at about 0.7 kg/m$^3$ which is much lower than the lowest amount standardized for new wood (4 kg/m$^3$). These results suggest that these three negative samples were either highly weathered or contained portions that were not arsenic treated.

Arsenic was also transferred from the surface of weathered wood or unweathered wood (4.0 kg/m$^3$ CCA), and detected in accordance with the "Dissolution Method" described above. A dry wipe made of polyester cloth was rubbed against the wood's surface; an area of about 50 cm×8 cm was covered repeatedly. The area and time of this wiping was not as important as the actual collection of wood residue on the wipe. The accumulation of residue was monitored visually by darkening of the portion of the wipe that was rubbed against the wood surface. Instead of adding wood to the vial to extract arsenic into solution, the wipe was added to the vial to transfer arsenic from the wood's surface and extract arsenic into solution. Color development of arsenic-treated weathered or unweathered wood took about 4 hours.

Example 2

Arsenic Stained on Wood

Untreated or non-arsenic preservative (e.g., borate, ACQ, CBA) treated wood was processed in accordance with the "Whole Wood Method" described above, but no staining was observed with a variety of wood types. There was development of a blue or blue-gray color only when wood treated with 4.0 kg/m$^3$ CCA preservative was processed. Color reached its maximum intensity in about 2 hours. PAN stain, however, was not arsenic specific. It resulted in a magenta color that reached its maximum intensity in about 30 seconds for CCA-treated wood.

REFERENCES

American Chemistry Council (ACS) (2003) Assessment of exposure to metals in CCA-preserved wood: Full study. Prepared by RIT International, Research Triangle Park, N.C.

TABLE 2

Field Trial Using Construction and Demolition (C&D) Wood

| | Prior Art Methods | | | | |
|---|---|---|---|---|---|
| | PAN Stain | Elements Detected by XRF (average, ppm) | | Type of Chemical Treatment | Reaction Time of Arsenic-Specific Stain |
| Sample | (+/−) | Cr | Cu | As | Preservative | |
| A | − | <216.3 | 174.7 | <10 | Borate | none |
| B | − | <205.3 | <35.7 | <9.3 | Borate | none |
| C | + | <284 | <34 | <10.3 | Untreated | none |
| D | + | <241.7 | <51.3 | <11.7 | Untreated | none |
| E | + | <261.3 | 10248 | <9.7 | Copper | none |
| F | + | <253.3 | 1481 | <18 | Copper | none |
| G | + | <263 | 6013 | <10 | ACQ | none |
| H | + | 9194.3 | 5412.3 | 6431.7 | CCA | 17 min 24 sec |
| I | + | 2526.3 | 1418.7 | 1476.3 | CCA | 37 min 42 sec |

American Wood Preservers' Association Standards (AWPA) (2003) American Wood Preservers' Association, Selma, Ala.

American Wood Preservers' Institute (AWPI) (1996) *Preserving Industry Production Statistical Reports*. American Wood Preservers' Institute, Fairfax, Va.

American Public Health Association (AHPA) (1995) *Standard Methods for the Examination of Water and Wastewater 19th Edition*. American Public Health Association, Washington D. C.

Blassino et al. (2002) Pilot scale evaluation of sorting technologies for CCA treated wood waste. Waste Management Research 20:290-301.

Chemical Specialties Inc. (CSI) (1995) ACQ Type D, Proposal to the AWPA Treatments Committee to Include ACQ Type D in Standards C2, C5, C9, and C15. CSI Inc., Charlotte, N.C.

Cooper (1993) Disposal of Treated Wood Removed From Service: The Issues. Proceedings of the Carolinas-Chesapeake Section of the Forest Products Society, Presented at the May 13, 1993 meeting on Environmental Considerations in the Use of Pressure-Treated Wood Products. Published by the Forest Products Society, Madison, Wis.

Cooper et al. (1995) Relating CCA fixation to leaching of CCA components from treated products. IRG/WP 95-50045; International Research Group: Stockholm, Sweden.

Cooper & Ung (1997) Effect of water repellents on Leaching of CCA from treated fence and deck units—An update, Document No. IRG/WP 97-50086. The International Research Group on Wood Preservation, Stockholm, Sweden.

Dang et al. (2003) *A Probabilistic Risk Assessment for Children Who Contact CCA-Treated Playsets and Decks*. U.S. Environmental Protection Agency, Office of Pesticide Programs, Washington D.C.

Feist & Ross (1995) Performance and durability of finish on previously coated CCA-treated wood. Forest Products Journal 45:29-36.

Homan & Militz (1994) Evaluation of Rapid Methods for Detecting Wood Preservatives in Waste Wood, IRG/WP 94-50024. International Research Group for Wood Preservation, Stockholm, Sweden.

Khan et al. (2004) Arsenic speciation of solvent-extracted leachate from new and weathered CCA-treated wood. Environmental Science and Technology 38:4527-4534.

Lebow et al. (2003) Effect of simulated rainfall and weathering on release of preservative elements from CCA-treated wood. Environmental Science and Technology 37:4077-4082.

Maas et al. (2002) Release of total chromium VI and total arsenic from new and aged pressure treated lumber. Technical Report #02-093. Environmental Quality Institute, University of North Carolina, Asheville, N.C.

Maas et al. (2004) Health effects of preserved wood: Relationship between CCA-Treated wood and incidence of cancer in the United States. Pre-Conference Proceedings of the "Environmental Impacts of Preservative-Treated Wood" Conference held in Orlando Feb. 8-11, 2004, pp. 17-31. Florida Center for Environmental Solutions, Gainesville, Fla.

McMurry (1992) *Organic Chemistry*. Brooks/Cole Publishing Company, Pacific Grove, Calif.

Micklewright (1998) *Wood Preservation Statistics 1997*. American Wood Preservers' Association, Granbury, Tex.

Milton (1995) *The Preservation of Wood: A Self Study Guide for Wood Treaters*. Minnesota Extension Service, University of Minnesota, College of Natural Resources.

Moskal (2001) *On-Line Sorting of Wood Treated with Chromated Copper Arsenate Using Laser Induced Breakdown Spectroscopy*. Master of Science Thesis, University of Florida, Gainesville, Fla.

Moskal & Hahn (2002) *On-line sorting of wood treated with chromated copper arsenate using laser induced breakdown spectroscopy*. Applied Spectroscopy 56:1337-1344.

Radziemski & Cremers (1989) *Laser-Induced Plasmas and Applications*. Marcel Dekker, New York, N.Y.

Roberts & Ochoa (2001) Memorandum to John Ruddell, Director of the Division of Waste Management, Florida Department of Environmental Protection. Florida Department of Environmental Protection, Tallahassee, Fla.

Ruddick & Xie (1994) Why does Douglas-fir heartwood turn black when treated with ammoniacal copper preservatives? Forest Products Journal 44:57-61.

Sandell & Onishi (1978) *Photometric Determination of Traces of Metals*. John Wiley & Sons, Toronto, Canada.

Shibata et al. (2004) Leachable and dislodgeable arsenic and chromium from in-service CCA-treated wood. Proceedings of the Environmental Impacts of Preservative Treated Wood Conference, Orlando Fla., pp. 335-351.

Solo-Gabriele & Townsend (1999) Disposal practices and management alternatives for CCA-treated wood waste. Waste Management Research 17:378-389.

Solo-Gabriele et al. (2001) On-Line Sorting Technologies for CCA-Treated Wood. Florida Department of Environmental Protection, Innovative Recycling Grants Program, Tallahassee, Fla. Available online at ccaresearch.org Solo-Gabriele et al. (2004) Evaluation of XRF and LIBS technologies for on-line sorting of CCA-treated wood waste. Waste Management 24:413-424.

Stalker (1993) Disposal of Treated Wood After Service. Paper presented to the Canadian Wood Preservation Association. Universal Forest Products. Grand Rapids, Mich.

Stilwell (1998) Arsenic from CCA-treated wood can be reduced by coating. Frontiers of Plant Science, pp. 6-8.

Stilwell & Gorny (1997) Contamination of soil with copper, chromium, and arsenic under decks built from pressure treated wood. Bulletin of Environmental Contamination and Toxicology 58:22-29.

Stilwell et al. (2003) Dislodgeable copper, chromium and arsenic from CCA-treated wood surfaces. The Science of Total Environment 312:123-131.

Stook et al. (2004) An evaluation of the heavy metal toxicity of pressure treated wood leachates with MetPLATE. Bulletin of Environmental Contamination and Toxicology 73:987-994.

Stook et al. (2005) Relative leaching and aquatic toxicity of pressure-treated wood products using batch leaching tests. Environmental Science and Technology 39:155-163.

Taylor et al. (1998) Effects of deck washes and brighteners on leaching of CCA. Treated Wood Research Group Research Bulletin 33:1-5.

Tolaymat et al. (2000) Chromated copper arsenate treated wood in recovered wood at construction and demolition waste recycling facilities. Environmental Engineering Science 17:19-28.

Townsend et al. (2003a) Chromium, copper, and arsenic concentrations in soil underneath CCA-treated wood structures. Soil & Sediment Contamination 12:1-20.

Townsend et al. (2003b) Impact of chromated copper arsenate (CCA) in wood mulch. Science of the Total Environment 309:173-185.

U.S. Consumer Products and Safety Commission (CPSC) (2003) Briefing Package, Petition to Ban Chromated Copper Arsenate (CCA)-Treated Wood in Playground Equipment (Petition HP 01-3).

U.S. Environmental Protection Agency (EPA) (2002) Notice of Receipt of Requests to Cancel Certain Chromated Copper Arsenate (CCA) Wood Preservative Products and Amend to Terminate Certain Uses of CCA Products. Federal Register 67:8244-8246.

U.S. Environmental Protection Agency (EPA) (2004) Question and Answers:

Draft Preliminary Probabilistic Risk Assessment for Children Who Contact Chromated Copper Arsenate (CCA) Treated Playsets and Decks. Last accessed Jul. 7, 2004 at EPA web site for Pesticides: Topical and Chemical Fact Sheets.

Weis & Weis (1995) Effects of chromated copper arsenate (CCA) pressure-treated wood in the aquatic environment. Ambio. 24:269-274.

Patents, patent applications, books, and other publications cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method of detecting arsenic, said method comprising:
    (a) extracting at least some arsenic from wood, which is suspected of being treated with preservative, into a solution;
    (b) combining at least ammonium molybdate and stannous chloride to form a stain, and standing for a time from about 5 minutes to one hour; and
    (c) mixing said solution with said stain to form a mixture; wherein development of a blue color in said mixture indicates the presence of arsenic.

2. The method of claim 1, wherein at least some arsenic is extracted from wood by dispersing sawdust, shredded wood, or wood chips in said solution.

3. A method of detecting arsenic, said method comprising:
    (a) transferring at least some arsenic from wood, which is suspected of being treated with preservative, to a wipe;
    (b) combining at least ammonium molybdate and stannous chloride to form a stain, and standing for a time from about 5 minutes to one hour; and
    (c) contacting said wipe with said stain to form a mixture; wherein development of a blue color in said mixture indicates the presence of arsenic.

4. The method of claim 1, wherein said ammonium molybdate is from 0.1 mM to 5 mM of said mixture.

5. The method of claim 1, wherein said stannous chloride is from 0.05 mM to 2.5 mM of said mixture.

6. The method of claim 1, wherein said color is developed over a time from 10 minutes to 6 hours.

7. The method of claim 1, wherein 2 milligrams of arsenate per liter of solution can be detected.

8. A method of detecting arsenic, said method comprising:
    (a) combining at least ammonium molybdate and stannous chloride to form a stain, and standing for a time from about 5 minutes to one hour; and
    (b) applying said stain on wood, which is suspected of being treated with preservative; wherein development of a blue color on said wood indicates the presence of arsenic.

9. The method of claim 8, wherein said stain is applied on an interior surface of said wood.

10. The method of claim 8, wherein said ammonium molybdate is from 2 mM to 100 mM of said stain.

11. The method of claim 8, wherein said stannous chloride is from 1 mM to 50 mM of said stain.

12. The method of claim 8, wherein said color is developed over a time from 10 minutes to 6 hours.

13. The method of claim 8, wherein 2 kilograms of arsenic-containing preservative per cubic meter of wood can be detected.

* * * * *